(12) United States Patent
Tsai et al.

(10) Patent No.: US 12,161,300 B2
(45) Date of Patent: Dec. 10, 2024

(54) ENCLOSED IMAGING APPARATUS AND METHOD FOR USE THEREOF

(71) Applicant: NinePoint Medical, Inc., New York, NY (US)

(72) Inventors: Tsung-Han Tsai, Newton, MA (US); Brian G. Connor, Bolton, MA (US); Jonathan Lawrence Goodwin, Nashua, NH (US); Eman Namati, Concord, MA (US)

(73) Assignee: NINEPOINT MEDICAL, INC., Austin, TX (US)

(*) Notice: Subject to any disclaimer, the term of this patent is extended or adjusted under 35 U.S.C. 154(b) by 0 days.

(21) Appl. No.: 17/112,740

(22) Filed: Dec. 4, 2020

(65) Prior Publication Data

US 2021/0169314 A1    Jun. 10, 2021

Related U.S. Application Data

(60) Provisional application No. 62/944,944, filed on Dec. 6, 2019.

(51) Int. Cl.
*A61B 1/04*    (2006.01)
*A61B 1/00*    (2006.01)
(Continued)

(52) U.S. Cl.
CPC .......... *A61B 1/041* (2013.01); *A61B 1/00078* (2013.01); *A61B 1/00135* (2013.01);
(Continued)

(58) Field of Classification Search
CPC ............ A61B 1/00073; A61B 1/00172; A61B 1/00183; A61B 1/041; A61B 5/0066; A61B 5/6861; A61B 2090/363; A61B 2090/3735
See application file for complete search history.

(56) References Cited

U.S. PATENT DOCUMENTS

2009/0209824 A1 * 8/2009 Korogi ................. A61B 5/0066
                                                            600/160
2009/0216079 A1   8/2009 Morgan et al.
                    (Continued)

FOREIGN PATENT DOCUMENTS

WO    WO-2018140683 A1 *  8/2018  ......... A61B 1/00117

OTHER PUBLICATIONS

PCT International Search Report dated Apr. 9, 2021, filed in PCT/US2020/063429, pp. 1-4.
(Continued)

*Primary Examiner* — Aaron B Fairchild
*Assistant Examiner* — Stephen Floyd London

(57) ABSTRACT

An exemplary capsule apparatus is provided, which includes a capsule having a first end and a second end opposite to the first end. A terminal portion of the capsule at the first end has a tapered end that has a section which curves toward a center of the terminal portion. Additionally, a tethered capsule apparatus includes a capsule configured to provide imaging optics having an orifice provided at least one end thereof. A tether having a proximal end and a distal end is also be provided. The distal end of the tether has an enlarged end portion that has a width that is greater than a width of a neighboring portion, and the enlarged end portion can be positioned and configured to be secured in the orifice.

11 Claims, 8 Drawing Sheets

(51) Int. Cl.
  *A61B 1/005* (2006.01)
  *A61B 90/00* (2016.01)
  *A61B 8/12* (2006.01)
(52) U.S. Cl.
  CPC .......... *A61B 1/00183* (2013.01); *A61B 1/005* (2013.01); *A61B 1/00009* (2013.01); *A61B 8/12* (2013.01); *A61B 90/39* (2016.02)

(56) References Cited

U.S. PATENT DOCUMENTS

| | | | |
|---|---|---|---|
| 2013/0310643 A1* | 11/2013 | Gora | A61B 1/00016 |
| | | | 600/109 |
| 2014/0228636 A1* | 8/2014 | Nimkar | A61B 1/00009 |
| | | | 600/109 |
| 2014/0243598 A1 | 8/2014 | Genier et al. | |
| 2015/0355413 A1* | 12/2015 | Bhagavatula | A61B 5/0084 |
| | | | 385/26 |
| 2017/0143196 A1* | 5/2017 | Liang | A61B 1/041 |
| 2018/0192863 A1* | 7/2018 | Yoshino | A61B 1/233 |
| 2019/0099237 A1* | 4/2019 | Booker | A61B 5/0084 |
| 2019/0142528 A1* | 5/2019 | Vertikov | A61B 8/12 |
| | | | 600/424 |
| 2020/0154985 A1* | 5/2020 | Ikuta | A61B 1/0623 |
| 2020/0297970 A1* | 9/2020 | Hamm | A61B 5/02007 |
| 2022/0142462 A1* | 5/2022 | Douk | A61B 1/00172 |
| 2022/0218206 A1* | 7/2022 | Petroff | A61B 5/6852 |

OTHER PUBLICATIONS

PCT Written Opinion dated Apr. 9, 2021, filed in PCT/US2020/063429, pp. 1-6.

* cited by examiner

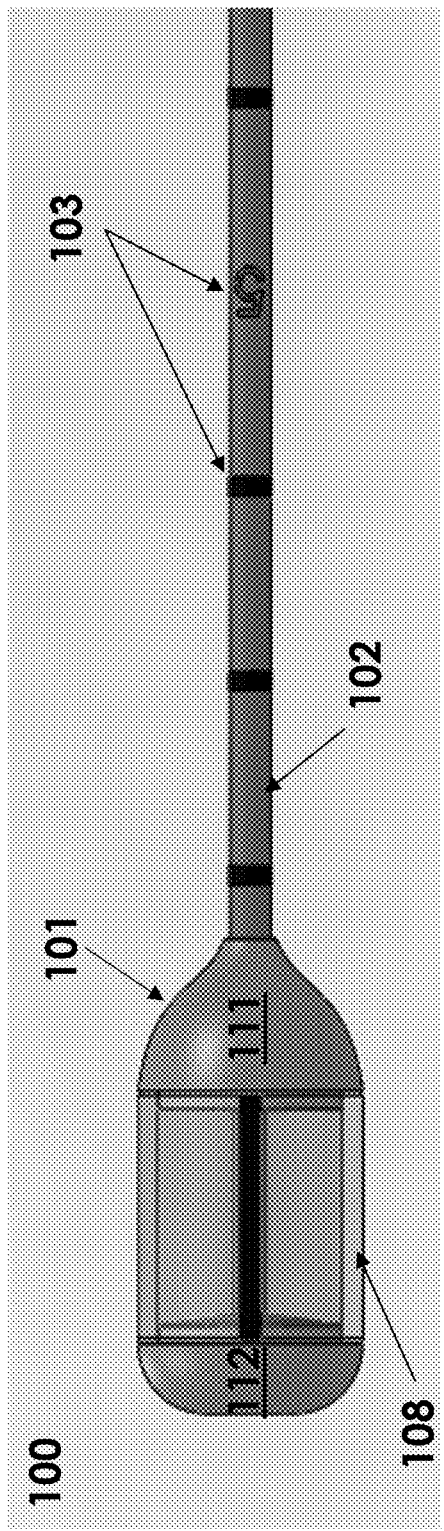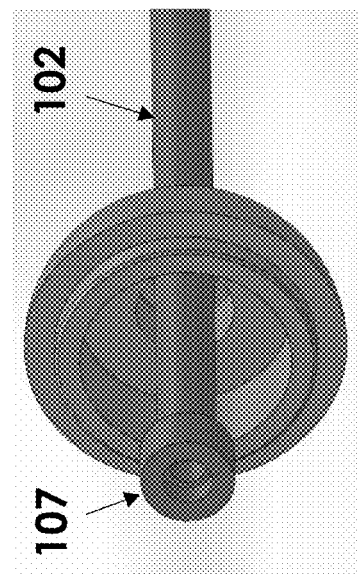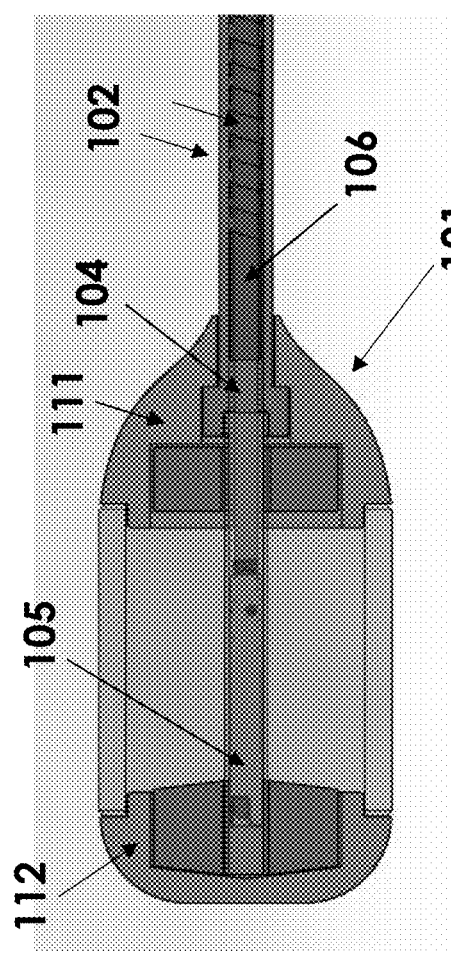
FIG. 1A
FIG. 1B
FIG. 1C

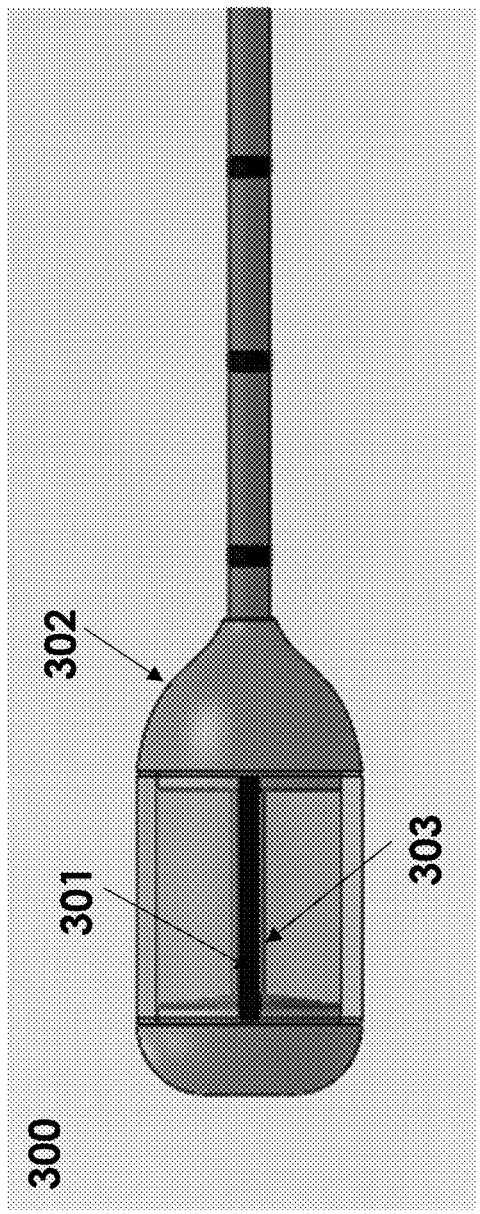
FIG. 3A
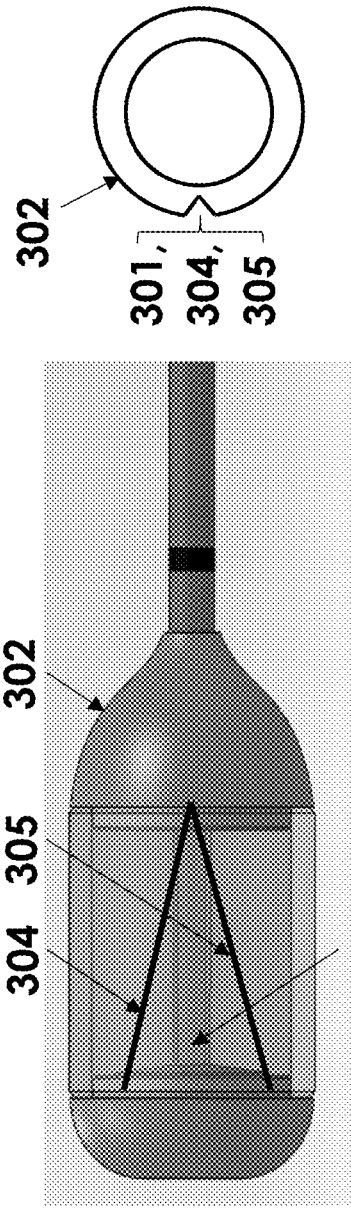
FIG. 3C
FIG. 3B

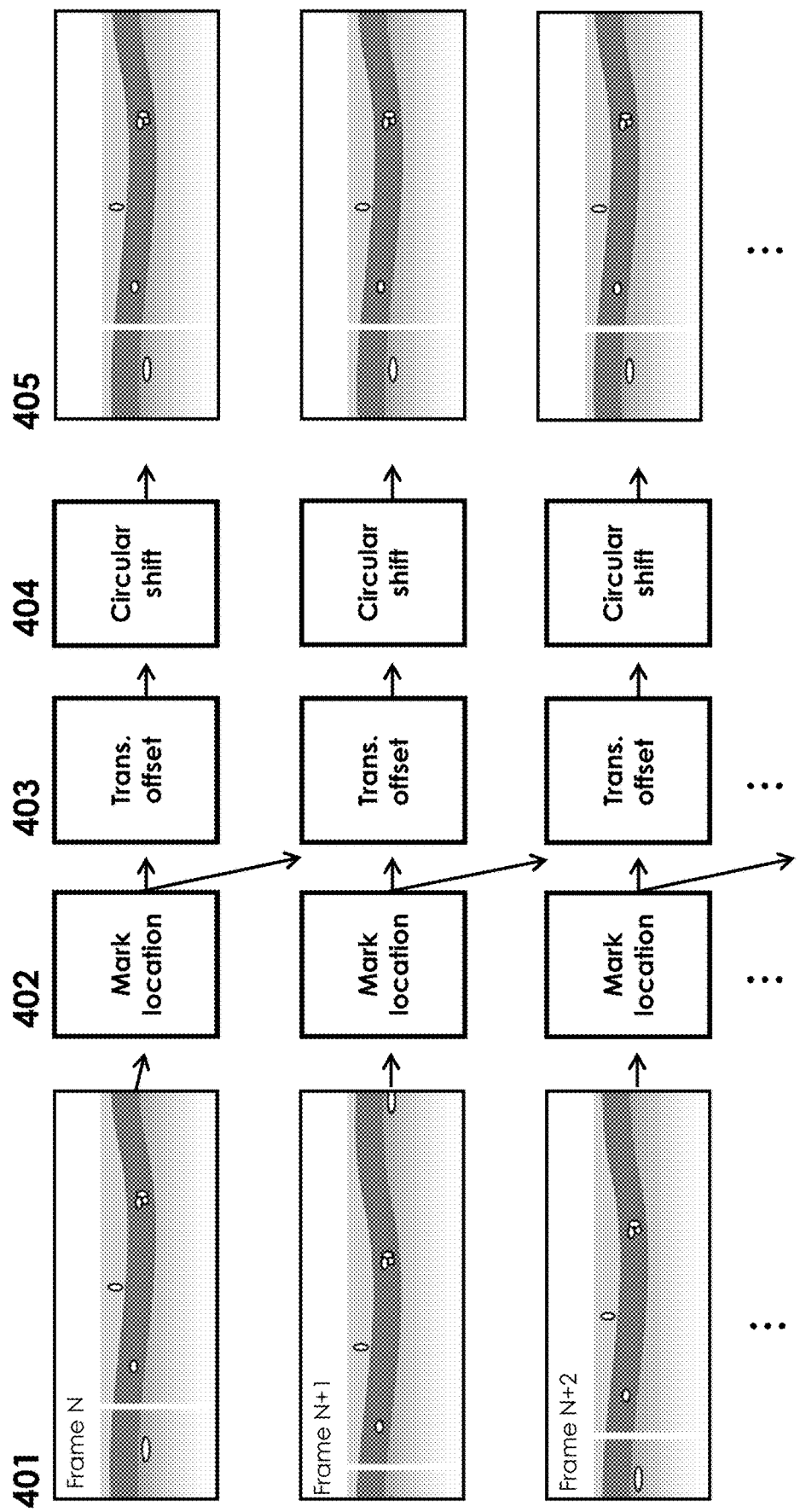

ENCLOSED IMAGING APPARATUS AND METHOD FOR USE THEREOF

CROSS-REFERENCE TO RELATED APPLICATIONS

The present disclosure is related and claims priority to U.S. Provisional Patent Application No. 62/944,944, entitled ENCLOSED IMAGING APPARATUS AND METHOD FOR USE THEREOF to Tsung-Han Tsai et al. filed on Dec. 6, 2019, the contents of which are hereby incorporated by reference, in their entirety, for all purposes.

FIELD

The present disclosure relates generally to an enclosed imaging apparatus and a method for use thereof, and more specifically, to exemplary embodiments of optical imaging probes and variants, and exemplary methods of production and the use thereof.

BACKGROUND

The performance of multiple imaging devices and optical procedures and/or modalities thereby, used for optical imaging of the interior of the body can be limited or inconsistent due to various factors, including, e.g., tissue motion, device scanning instability, device robustness, inter-operator variation, or combinations thereof. It is with respect to these and other considerations that the present improvements are needed. Thus, it may be beneficial to provide exemplary apparatuses, devices, systems and methods, which can address and/or overcome at least some of the above-described deficiencies.

SUMMARY

To that end, such exemplary apparatuses, devices, systems and methods can be provided according to embodiments of the present disclosure which can address and/or overcome at least the above-described deficiencies and others.

In one embodiment, an imaging apparatus includes a capsule having a first end and a second end opposite to the first end, wherein a terminal portion of the capsule at the first end has a tapered end that has a section that curves toward a center of the terminal portion. The imaging apparatus includes a sheath, mechanically coupled with the first end, and associated with a catheter body, and an imaging element positioned between the first end and the second end, the imaging element being configured to provide an imaging radiation to a distal tissue, and to collect a scattered radiation from the distal tissue. The imaging apparatus also includes a functional marking feature disposed on the capsule, the marking feature configured to provide at least one fiducial mark for each full rotation of the imaging element in an image formed with the scattered radiation.

In a second embodiment, a method of forming an image with an imaging apparatus includes collecting a first image and a second image with a capsule imaging system, the first image and the second image including a fiducial mark indicative of a spatial feature. The method also includes comparing the fiducial mark in the first image to the fiducial mark in the second image to determine a magnitude of the spatial feature. The method also includes adjusting a longitudinal position of an imaging device within the capsule imaging system with an actuator to correct for an artifact causing the spatial feature and applying a correction factor to a digital file including one of the first image and the second image, based on the spatial feature.

Thus, according to an exemplary embodiment of the present disclosure, an exemplary capsule imaging apparatus and use, production, and operation thereof. Various exemplary implementations of the capsule imaging apparatuses implement optical coherence tomography (OCT) and/or optical frequency domain imaging (OFDI) gastrointestinal tissue imaging methods and technologies. Furthermore, the exemplary imaging apparatuses according to an exemplary embodiment of the present disclosure can include a rotatable imaging element to scan a bodily lumen, such as the esophagus. In a further exemplary embodiment of the present disclosure, the exemplary imaging apparatuses may include a shaped tip. The shaped tip can facilitate, at least in part, guiding of the exemplary imaging apparatus through the esophagus, and/or other bodily lumen. Mechanical and registration features of the imaging apparatuses can provide a way for enhancing imaging performance via signal processing methods.

To that end, an exemplary capsule apparatus can be provided, which can include a capsule having a first end and a second end opposite to the first end. A terminal portion of the capsule at the first end can have a tapered end that has a section which curves toward a center of the terminal portion. Additionally, a tether can be provided that is connected to the first end and/or the second end. According to other exemplary embodiments, the first and second ends can be free of a tether.

According to still another exemplary embodiment, a tethered capsule apparatus is provided, which can include a capsule configured to provide imaging optics having an orifice provided at least one end thereof. A tether having a proximal end and a distal end can also be provided. The distal end of the tether can have an enlarged end portion that has a width that is greater than a width of a neighboring portion, and the enlarged end portion can be positioned and configured to be secured in the orifice. For example, the width of the enlarged end portion can be greater than a width of the orifice that is provided internally in the capsule. Further, a mechanical interaction between the enlarged end portion and the orifice can provide a mechanical interference therebetween.

In yet another exemplary embodiment, an enclosure arrangement is provided for an optical drive shaft. Such an exemplary enclosure arrangement includes a cover that has a first portion which is more flexible than a second portion of the cover which is adjacent to the first portion. The cover can be configured to at least partially enclose the optical drive shaft. An outer sleeve can be provided that at least partially encloses the cover. The cover can include a lubricious material that facilitates a rotation and/or a translation of the optical drive shaft. At least one portion of the cover can have ridges and/or grooves with at least approximately a helical configuration.

In another exemplary configuration, the ridges and/or the grooves are provided along the cover, and the ridges and/or the grooves can have an alternating configuration in a longitudinal direction. In still another exemplary configuration, the ridges and/or grooves can extend continuously and fully around an outer periphery of the cover. Further, the ridges and/or the grooves can have a pitch that is greater in the first portion than in the second portion. The cover can include a third portion, whereas the first portion can be provided between the second and third portions, and the third portion can be more flexible than the first portion.

According to a further embodiment of the present disclosure, an enclosure arrangement is provided for an optical drive shaft. The exemplary enclosure arrangement can include a cover that has a first portion which is rigid, and a second portion which is flexible. The cover can extend along a longitudinal direction and at least partially covers the optical drive shaft, and the first and second portions can extend along the longitudinal direction.

In another embodiment, a tethered capsule apparatus is provided which includes imaging optics, and a capsule configured to provide therein the imaging optics and having an orifice provided at least one end thereof, whereas the capsule can include a marking configuration. A tether can also be provided that is connected to the imaging optics, as well as a controller which is configured to receive imaging information from the imaging optics via the tether. The controller can determine a degree of tension of the tether based on the imaging information using the marking configuration. The controller can also determine a force measurement on the tether based on the imaging information.

These and other objects, features, and advantages of the exemplary embodiments of the present disclosure will become apparent upon reading the following detailed description of the exemplary embodiments of the present disclosure, when taken in conjunction with the appended paragraphs.

BRIEF DESCRIPTION OF THE DRAWINGS

Further objects, features, and advantages of the present disclosure will become apparent from the following detailed description taken in conjunction with the accompanying figures showing illustrative embodiments of the present disclosure, in which:

FIG. 1A is a side view of an exemplary capsule imaging apparatus according to an exemplary embodiment of the present disclosure.

FIG. 1B is a cross-sectional view of a distal portion of the exemplary capsule imaging apparatus shown in FIG. 1A.

FIG. 1C is a perspective view of the distal portion of the exemplary capsule imaging apparatus shown in FIG. 1A, with a cover removed therefrom to illustrate internals portion thereof.

FIG. 3A is a side view of an exemplary capsule imaging apparatus according to another embodiment of the present disclosure.

FIG. 3B is a side view of another exemplary capsule imaging apparatus of the present disclosure.

FIG. 3C is a cross-sectional view of the distal portion of another exemplary capsule imaging apparatus of the present disclosure.

FIG. 4A is a diagram of a first portion of an exemplary method that uses image data produced by the capsule imaging apparatus according to various embodiments of the present disclosure with registration markers to improve image quality, according to further embodiments of the present disclosure.

Figure 2:
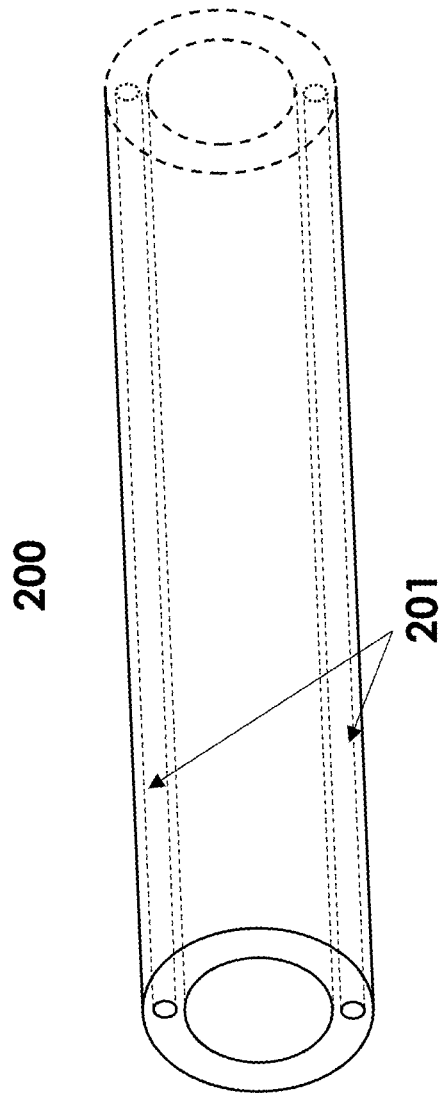
FIG. 2 is a perspective view of a reinforced sheath for the exemplary capsule imaging apparatus according to an exemplary embodiment of the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures and the appended paragraphs.

DETAILED DESCRIPTION

The embodiments of the present disclosure may be further understood with reference to the following description and the related appended drawings. As used herein, the devices can be used on a person (e.g., a human). However, the devices can also be used for other subjects including, but not limited to, animals or other various species.

MRI, x-ray, ultrasound, and optics have all found important roles in imaging applications. In many applications optical radiation to effectuate imaging, analysis, therapy, and other applications can offer certain advantages over other approaches. There are a variety of types of optical techniques which utilize optical (e.g., light) radiation delivery, that are currently available including, e.g., optical coherence tomography (OCT) and other interferometric imaging techniques.

Optical imaging of the interior of the body is often used to assess tissue structures and anatomy. Examples of optical imaging techniques are optical coherence tomography (OCT), angioscopy, near infrared spectroscopy, Raman spectroscopy, and fluorescence spectroscopy. Other exemplary methods/procedures include confocal, multi-photon, and spectrally-encoded confocal microscopy (SECM). Some of these and other exemplary applications can include intravascular OCT (as described in, e.g., Bouma et al., "Intravascular optical coherence tomography," Biomedical Optics Express 2660, Vol. 8, No. 5, May 1, 2017), optical spectroscopy (as described in, e.g., Utzinger et al., "Fiber Optic Probes For Biomedical Optical Spectroscopy," J. of Biomedical Optics, 8(1), (2003)), and cardiac ablation (as described in, e.g., Dukkipati et al., "Pulmonary Vein Isolation Using The Visually Guided Laser Balloon: A Prospective, Multicenter, And Randomized Comparison To Standard Radiofrequency Ablation," JACC, 66(12):1350-60 (2015)). Other exemplary techniques include, e.g., other spectroscopic imaging techniques, Raman imaging, diffuse-wave optical imaging, and two-photon imaging techniques. OCT is an interferometric imaging technology and thus has the properties of very high sensitivity and large dynamic range. OCT achieves depth resolution via a combination of the focal properties of the imaging optics used and the coherence properties of the optical source used.

Typically, devices for optical imaging of the interior of the body include an imaging end (e.g., distal end) functionally coupled to an operating end (e.g., proximal end). The imaging end, which is inserted into the body, is typically operated and manipulated by the operating end, which is accessible to an external operator.

One exemplary device for optical imaging of the interior of the body is a capsule endoscope. Capsule endoscopes may include an imager, at least one illumination source, and an optical system. Capsule endoscopes may also include other sensors which can sense the in vivo environment, such as temperature sensors, position sensors, motion sensors, pH sensors, and pressure sensors.

In some examples, the esophagus is used as a bodily lumen. However, this is not intended to be limiting. Furthermore, the various depictions are not drawn to scale. Instead, they are drawn in a manner to facilitate understanding. Additionally, the various examples and illustrations can be combined with each other, even where not specifically so stated. Additionally, the described examples are not intended to limit the claims and the present disclosure.

FIGS. 1A-1C illustrate various views of an exemplary capsule imaging apparatus 100 according to an embodiment of the present disclosure. The exemplary capsule imaging apparatus 100 can be used to implement various optical modalities and technologies, including but not limited to optical coherence tomography (OCT) and/or optical frequency domain imaging (OFDI) gastrointestinal tissue for imaging and obtaining other information. Other modalities which can be implemented by the exemplary imaging apparatus 100 can also include other scanning optical imaging modalities, such as, e.g., visible light, fluorescence, confocal, or the like, or non-optical imaging modalities, such as ultrasound. In one implementation, the exemplary imaging apparatus 100 includes a system utilizing OCT and/or OFDI modalities. For example, the exemplary imaging apparatus 100 can be configured to detect at least one type of electromagnetic radiation, such as, e.g., a back reflected light, from one or more portions associated with tissue. The detected electromagnetic radiation can be processed by the exemplary imaging apparatus 100 and/or a system connected thereto to ascertain information, such as microstructures, associated with the tissue.

In one exemplary implementation, the capsule imaging apparatus 100 includes a proximal system including, e.g., optical fiber, data processing and associated data storage, and the like. As is illustrated in FIG. 1A, the exemplary capsule imaging apparatus 100 includes a shaped tip 101 located at the distal end of imaging apparatus 100. The inclusion of the shaped tip 101 facilitates guiding of the exemplary imaging apparatus 100 through the esophagus or any other anatomical lumen. The shaped tip 101 can also facilitate guiding of the exemplary imaging apparatus 100 to a desired position within the anatomical lumen. A proximal portion 111 of the shaped tip 101 is illustrated in FIG. 1A as being tapered, and other shapes of the tip 101 are within the present disclosure. The shaped tip proximal taper may serve to more easily and smoothly pull the capsule imaging apparatus 100 through anatomical restrictions such as the lower esophageal stricture (LES). The distal portion 112 of the shaped tip 101 is illustrated in FIG. 1A as being blunted, though other shapes are possible. The blunted distal portion of the shaped tip 101 can reduce the overall rigid length of the shaped tip 101, and better accommodate the anatomical motion, such as, e.g., peristalsis. For example, as indicated herein above, the shaped tip 101 can have other smooth shapes and provide a different shape on the distal or proximal side. The shaped tip 101 can be made of a polymer, such as, e.g., polyamide, polyurethane, nylon, polyethylene, polyether block amide, polyester, polycarbonate, polypropylene, acrylonitrile-butadiene styrene terpolymer, polyetheretherketone (PEEK), or the like. Alternatively or in addition, the shaped tip 101 can also be made of a non-polymer, such as glass, metal, or the like.

As shown in FIGS. 1A-1C, the exemplary capsule imaging apparatus 100 can include a sheath 102 which can be generally associated with a catheter body. The sheath 102 can house a torque coil 104 which facilitates rotation of an imaging element 105 (including but not limited to, e.g., a ball lens, a graded-index fiber lens, a micro-lens, a phase array, and a curved mirror) associated with the distal portion of the torque coil 104. The imaging element 105 can be coupled to a fiber optic line which can be contained or housed within the sheath 102. The fiber optic line can be coupled to a portion of the imaging apparatus 100 that facilitates the implementation of OCT and/or OFDI methods and technologies, as well as other modalities, methods, and/or technologies. The imaging element 105 can be configured and/or programmed for circumferential scanning using, e.g., at least the rotatable torque coil 104. The imaging element 105 can also be configured to manipulate, direct, and/or focus an imaging beam onto the tissue. A window 108 may protect the interior of imaging apparatus 100, while being transparent or semi-transparent to the radiation provided by the imaging element 105 to the tissue, and to the scattered radiation from the tissue to the imaging apparatus 100. According to an embodiment of the present disclosure, light or other electro-magnetic radiation reflected from the tissue may be received and/or processed by the imaging element 105, and conveyed to computer processing system(s) associated with the imaging apparatus 100, e.g., via an fiber optic line, or the like. In another implementation, the reflected light or other electro-magnetic radiation reflected from the tissue can be conveyed wirelessly to the data processing systems associated with the imaging apparatus 100. In another implementation, the circumferential scanning of the imaging beam transmitted via the imaging element 105 can be performed using at least one distal actuator, such as, e.g., a micro-motor and microelectromechanical system (MEMS) scanner.

As shown in FIG. 1A, the sheath 102 can include depth markings 103, which can be viewed by the users to indicate the longitudinal location of the shaped tip 101 in the bodily lumen. Depth markings 103 can be positioned on an inner surface or an outer surface of sheath 102, and/or within the wall thickness of sheath 102. A depth marking 103 can include one or more markers, e.g., oriented perpendicular to a longitudinal axis of the sheath 102. The depth marking 103 can be positioned circumferentially and visible from all viewing directions, or positioned partially on the circumference of sheath 102 so that it is visible from a limited range of viewing directions.

FIG. 1B illustrates a cross-sectional view of a distal portion of the exemplary capsule imaging apparatus 100, according to some embodiments. In some embodiments, capsule imaging apparatus 100 includes a spiral cut bearing tube 106. In some embodiments, the spiral cut bearing tube 106 covers the torque coil 104, and is situated inside the sheath 102. The spiral cut bearing tube 106 can be cut at various pitch distances and angles, or remain uncut for various distances along the sheath length, resulting in different mechanical properties, such as, e.g., flexibility, rigidity, or the like. The spiral cut bearing tube 106 can include a low friction bearing surface between the sheath 102 and the torque coil 104 and facilitate support in straight or curved configurations of the sheath 102. In some embodiments, the spiral cut bearing tube 106 can be made of a polymer, such as polyimide, PEEK, polytetrafluoroethylene, polyester, or the like.

FIG. 1C illustrates a mechanical interlock configuration/structure 107 in the capsule imaging apparatus 100, according to some embodiments. The mechanical interlock configuration/structure 107 can connect or otherwise join the sheath 102 to the proximal end of shaped distal tip 101. The mechanical interlock configuration/structure 107 can be, e.g., thermoformed as part of the sheath 102, or provided as a separate component that can be adhesively bonded to the sheath 102 and/or the shaped distal tip 101. In some embodiments, the mechanical interlock configuration/structure 107 strengthens the capsule-to-sheath connection, in addition to having an adhesive seal between the sheath 102 and the shaped distal tip 101.

FIG. 2 illustrates a perspective view of a reinforced sheath 200 for a capsule imaging apparatus according to an embodiment of the present disclosure (e.g., capsule imaging apparatus 100). The reinforced sheath 200 can replace and/or be combined with the exemplary sheath 102 (cf. FIGS. 1A-1C). One or more strength members 201 can be positioned on an outer surface of the sheath 200, imbedded in the sheath material, and/or fit within lumens in the sheath wall. The material of the strength members 201 can be or include metal, composite, or plastic. The strength members 201 can act as tensile stiffener members for the reinforced sheath 200, e.g., reducing stretch while under a tensile load.

FIGS. 3A-3C illustrate various views or portions of another exemplary capsule imaging apparatus 300 with registration markers according to another embodiment of the present disclosure. The capsule imaging apparatus 300 can utilize and/or implement optical coherence tomography (OCT) and/or optical frequency domain imaging (OFDI) gastrointestinal tissue imaging methods and technologies. Alternatively or in addition, the exemplary imaging apparatus 300 can implement other scanning optical imaging modalities, such as white light, fluorescence, confocal, or the like. Furthermore, the exemplary imaging apparatus 300 can implement other tissue imaging methods and technologies. In one implementation, the exemplary imaging apparatus 300 includes a system which utilizes at least one of OCT or OFDI modalities. In some embodiments, imaging apparatus 300 is configured to receive and/or detect electromagnetic radiation, such as back reflected light, from one or more portions associated with the tissue. The detected electromagnetic radiation can be processed by the imaging apparatus 300 to ascertain information, such as microstructures associated with the tissue.

The exemplary capsule imaging apparatus 300 can include one or more registration markers 301 positioned to be viewed by capsule imaging apparatus 300. The registration marker(s) 301 can be associated with the electromagnetic radiation detected and processed by the exemplary capsule imaging apparatus 300. Registration marker(s) 301 can be positioned on an inner surface and/or an outer surface of a shaped tip 302 (cf. shaped tip 101), or within the wall thickness of the shaped tip 302. The registration marker(s) 301 can include one or more markers oriented parallel to a longitudinal axis of the shaped tip 302. Registration marker(s) 301 can be positioned to be viewed at least once for each 360° rotation of an imaging element 303 (e.g., similar to imaging element 105), and can be included in each cross-sectional image of the bodily lumen produced by the exemplary capsule imaging apparatus 300. Such configurations can be used, and are, thus, functional, to modify and/or correct the frame-to-frame transverse offset introduced by the imaging element 303 scanning instability. Such registration marker(s) 301 can be placed along a circumference of the shaped tip 302 with fixed angles from one of the registration marker(s) 301, so as to register the image and/or to determine a variation in an angular velocity of the exemplary imaging assembly, which can reduce a non-uniform rotational distortion (NURD).

FIG. 3B shows an enlarged view of the distal portion of the exemplary capsule imaging apparatus 300. As illustrated in FIG. 3B, the exemplary capsule imaging apparatus 300 can further include one or more further registration markers 304, 305 positioned on an inner or outer surface of the shaped tip 302, or within the wall thickness of the shaped tip 302. Such further, functional registration marker(s) 304, 305 can include one or more markers oriented along a partial circumference of the shaped tip 302. The further registration marker(s) 304, 305 can be positioned to be viewed by the imaging element 303. Such positioning of the further registration marker(s) 304, 305 facilitates determining the distance between one or more of the further registration marker(s) 304, 305, e.g., when the imaging element 303 is at different longitudinal positions during the operation when the capsule imaging apparatus 300 is configured to produce three-dimensional images of the bodily lumen. Exemplary images, including representations of at least one or more of the further registration markers 304, 305, can be correlated to the specific location of the imaging element 303 inside the shaped tip 302 to which they are positioned, so as to provide longitudinal registration information for one or more exemplary images produced by the exemplary capsule imaging apparatus 300. Further longitudinal imaging registration can be performed by correlating a second image generated subsequent to the first image. For example, the first image can include a representation of one or more of the further registration markers 304, 305, and the longitudinal position of the second image can be determined by accounting for a longitudinal translation of the imaging element 303.

One or more of the exemplary registration markers 301, 304, and 305 can be used singly or in combination with one another to provide registration information between one or more images generated by the exemplary capsule imaging apparatus 300. Alternatively or additionally, one or more of the registration markers 301, 304, and 305 can be used singly or in combination to position (e.g., to advance, retract, and/or rotate) the exemplary capsule imaging apparatus 300. One or more of the exemplary registration markers 301, 304, and 305 can be positioned at known radial or longitudinal offsets, such that when viewed in one or more images, the known offset provides the registration or other data. One or more of the exemplary registration markers 301 and 304, 305 can be constructed or arranged to provide the registration or other data of the first image to the second image, and the registration or other data of the first image to one or more portions of the bodily lumen.

One or more of the exemplary registration markers 301, 304, and 305 can include material that can be configured to absorb, reflect or scatter one or more forms of electromagnetic radiation. In one exemplary implementation, one or more of the exemplary registration markers 301, 304, and 305 can be reflective or absorptive to infrared light, e.g., the infrared light can be used by the capsule imaging apparatus 300. Alternatively or additionally, one or more of the exemplary registration markers 301, 304, and 305 can be reflective or absorptive to visible light, such as visible light used by the exemplary capsule imaging apparatus 300. One or more of the exemplary registration markers 301, 304, and 305 can be configured to scatter light, such as visible or infrared light.

FIG. 3C illustrates one or more registration markers 301, 304, and 305, on the shaped tip 302, according to some embodiments. One or more of the exemplary registration markers 301, 304, and 305 can include one or more components such as, a wire, a metal foil, a metal strip, an ink, a dye, and combinations thereof. In some embodiments, one or more of registration markers 301, 304, and 305 can be structural features on an inner or outer surface of the capsule shell, or provided within the wall thickness of a shaped tip 302, such as, for example, a bump, a notch, a ramp, a change of wall thickness, and combinations thereof. In one implementation, the shaped tip 302 with one or more of the exemplary registration markers 301, 304, and 305 can introduce one or more tissue deformation projections, whereas the deformed tissue can provide image registration or other data. In some embodiments, the capsule imaging apparatus 300 can include an ultrasound imaging device, whereas one or more of the registration markers 301, 304, and 305 can absorb, reflect, or scatter ultrasound.

Figure 4B:
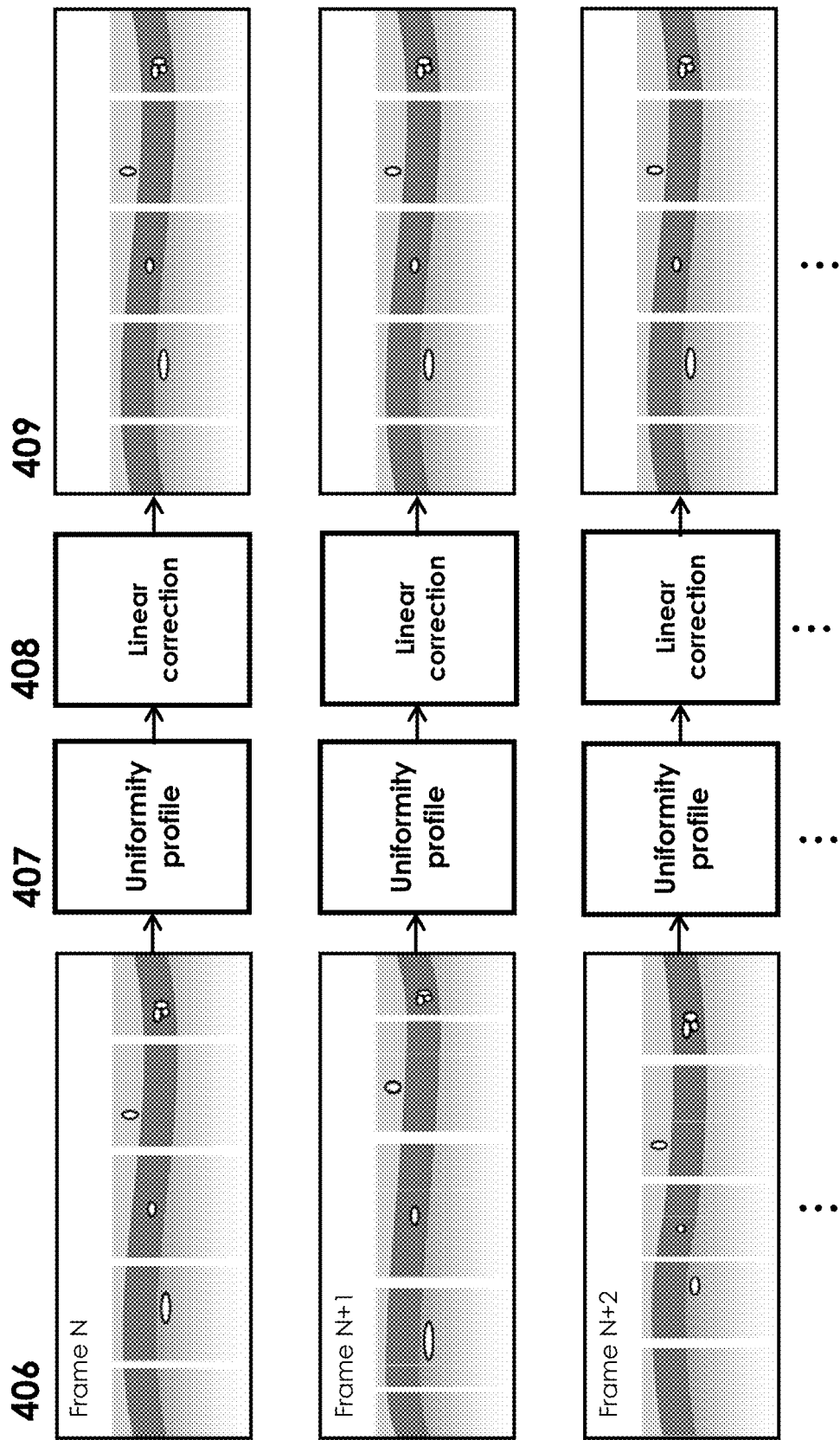
FIG. 4B is a diagram of a method provided to reduce the non-uniform rotational distortion (NURD) according to another embodiment of the present disclosure.

FIGS. 4A and 4B show a set of diagrams of exemplary procedures of methods according to an embodiment of the present disclosure that can utilize the image data produced by capsule imaging apparatus 300 to improve the quality of the images. An image quality improvement can include, but is not limited to, the reduction of a degradation associated with the mechanical interactions between the scanner and image assembly such as frame-to-frame transverse offset, non-uniform rotational distortion (NURD), and combinations thereof.

FIG. 4A shows a diagram of an exemplary method to correct the frame-to-frame transverse offset, in which a series of raw image frames 401 (e.g., 'frame N,' 'frame N+1,' and 'frame N+2') produced by the exemplary capsule imaging apparatus 300 can be generated to detect a registration mark location 402 for each frame. The transverse offsets 403 for each frame can be determined based on the difference of the registration mark locations between the neighboring frames. Each raw image frame 401 can then be circularly shifted 404 along the transverse direction in accordance to the corresponding offset 403, and the corrected frame 405 can then be generated.

FIG. 4B illustrates a method to reduce the non-uniform rotational distortion (NURD). In some embodiments, a series of raw image frames 406 produced by the capsule imaging apparatus 300 can be processed to calculate and/or otherwise provide the uniformity profiles 407 based on one or more registration marks in each image frame. In some embodiments, the distance between the two neighboring registration marks is used to assess a NURD artifact in the image. In some embodiments, a transverse location of one or more registration marks in the image frame may indicate a transverse offset. In other embodiments, a combination of a NURD and a transverse offset artifact may be assessed using one or more registration marks, as disclosed herein. A linear correction 408 along the transverse direction of the image frame in accordance to the uniformity profile can then be performed to minimize or otherwise reduce the NURD and generate the corrected frames 409. An example of the linear correction 408 is interpolating the image pixels along the transverse direction to convert the uniformity profile into a linear profile. Another example of the linear correction 408 is providing or generating a pixel look-up table based on the non-uniformity profile and remapping the image pixels along the transverse direction.

Figure 5:
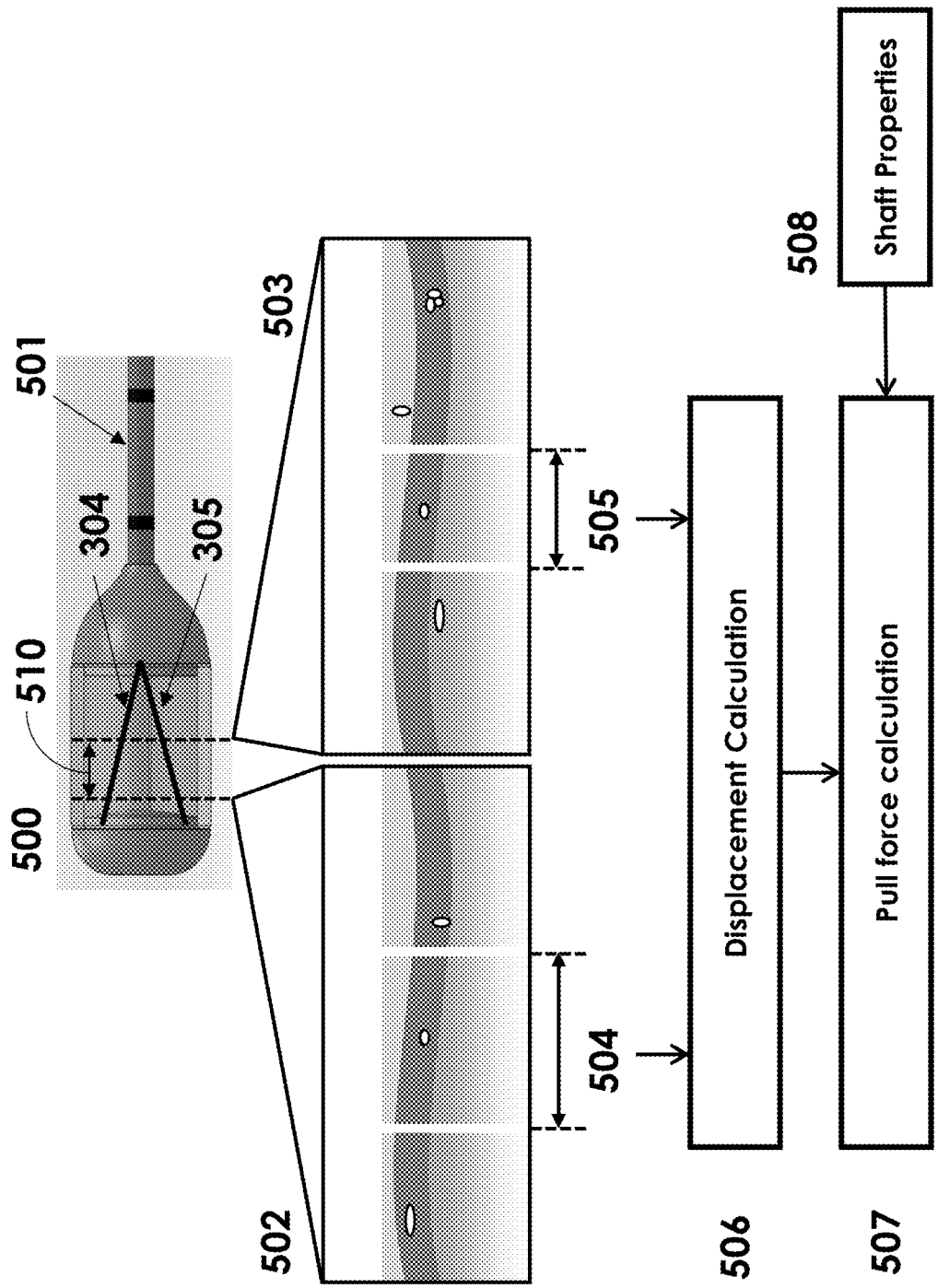
FIG. 5 is a diagram illustrating exemplary procedures utilized in method that uses the image data produced by the exemplary capsule imaging apparatus according to various embodiments of the present disclosure with the registration markers to indicate the longitudinal displacement of the image assembly and the pull force along the capsule sheath, according to further embodiments of the present disclosure.

FIG. 5 illustrates a diagram of a method according to a another embodiment of the present disclosure that uses the image data produced by capsule imaging apparatus 500 with registration markers 304 and 305 to indicate a longitudinal displacement 510 of the capsule imaging apparatus 500 in the shaped tip and the pull force along a sheath 501. In some embodiments, the capsule imaging apparatus 500 includes different distance between its markers or different width of a marker at a different longitudinal location on the shaped tip thereof. Without applying force to the sheath 501 or introducing displacement of the imaging element in the capsule imaging apparatus 500, the distance 504 between the registration marks and/or the width of the registration marks 304 and 305 can be measured from an image 502 produced by the exemplary capsule imaging apparatus 500. Upon an application of a pull force along the sheath 501, the distance 505 between registration marks 304 and 305 can be measured from an image 503 produced by the exemplary capsule imaging apparatus 500. In some embodiments, a displacement calculation 506 determines a longitudinal displacement 510 of the imaging assembly, based on the measurements 504 and 505, as described herein. Since the displacement 510 of the imaging element can be caused by the elongation of the sheath 501, a pull force calculation 507 along the sheath 501 can be calculated or otherwise determined based on the longitudinal displacement calculation 506 of the imaging element or the mechanical properties of the capsule shaft 508, such as the elastic modulus of the sheath material.

Figure 6:
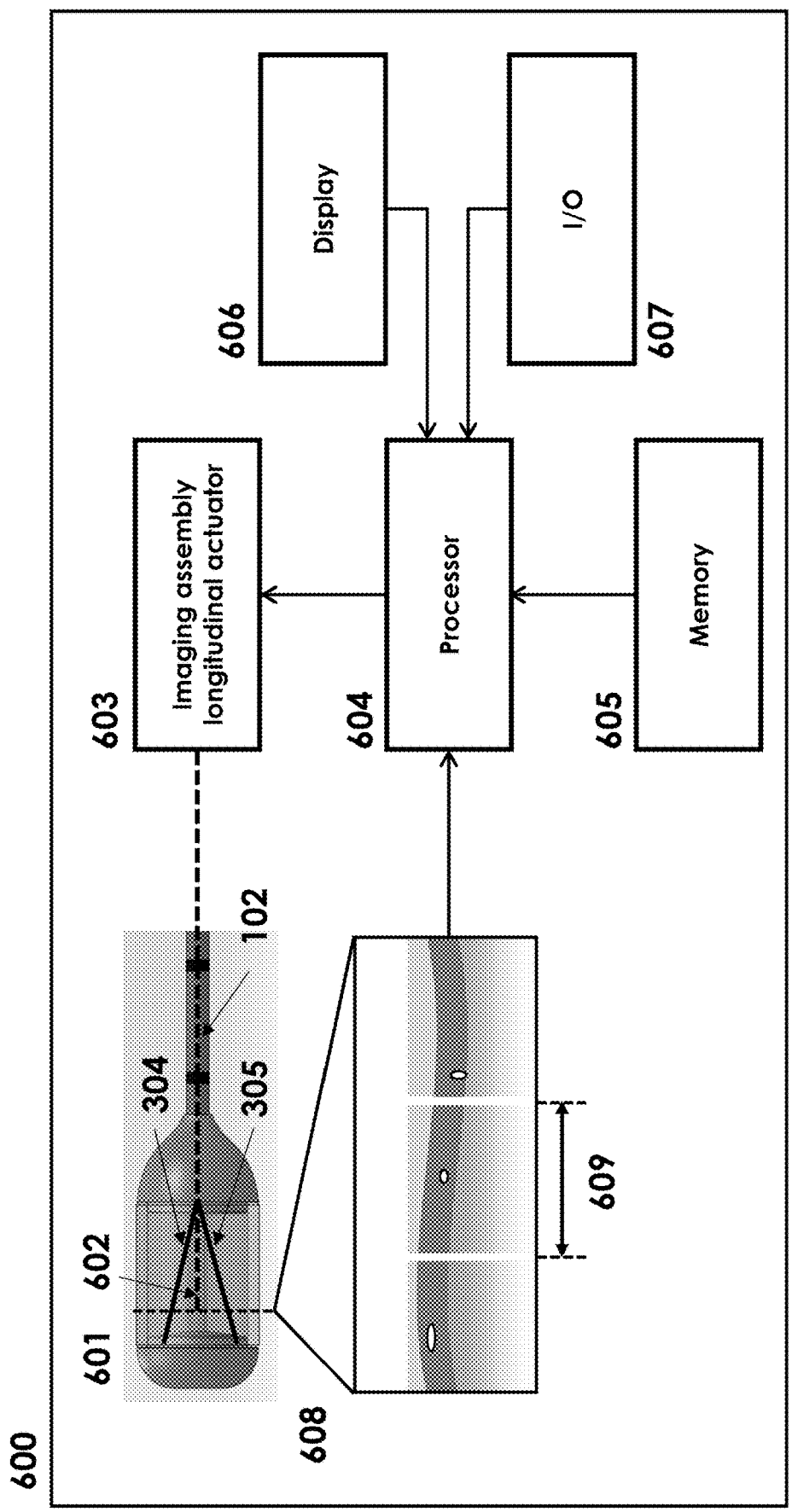
FIG. 6 is a diagram of an exemplary capsule imaging system which utilizes the capsule imaging apparatus according to various embodiments of the present disclosure, and provides procedures utilized in a method that compensates for the longitudinal displacement of the image element, according to further embodiments of the present disclosure.

FIG. 6 illustrates a diagram of a capsule imaging system 600 according to an embodiment of the present disclosure. For example, using the capsule imaging system 600, it is possible to compensate for a longitudinal displacement of the image assembly in the capsule shell using a longitudinal actuator 603. The capsule shaped tip 601 can have a different distance between the markers 304 and 305 and/or a different width of a marker at different longitudinal locations on the shaped tip 601. An imaging element 602 can be attached or otherwise connected to the longitudinal actuator 603, which may be provided proximally or distally with respect to the capsule shaped tip 601. In some embodiments, the longitudinal actuator 603 controls the longitudinal position of the imaging element 602 inside the shaped tip 601. In some embodiments, the capsule imaging system 600 includes a computer processor 604 configured to receive signals from the capsule imaging element 602. Additionally, in some embodiments, the capsule imaging system 600 includes a data storage device (e.g., a memory 605) in communication with the computer processor 604. A data storage device 605 (e.g., a memory circuit, such as a random access memory RAM, a dynamic RAM, DRAM, or a static RAM, SRAM, and the like) can include programs for controlling the longitudinal actuator 603 and processing the multiple images 608 produced by the capsule imaging element 602, as well as storing processed and/or raw image data produced by the capsule imaging element 602. In some embodiments, the capsule imaging system 600 includes a display 606 for displaying the images produced by the imaging element 602. In some embodiments, the computer processor 604 can orient or scale the display 606 to properly process and/or register the images 608, accordingly. In addition, although illustrated as one display 606, more than one display can be implemented and/or utilized. In some embodiments, the capsule imaging system 600 includes input/output (I/O) devices 607 such as, a keyboard, a touch screen, a mouse, and a remote controller to provide additional control over the components of the system.

In some embodiments, upon applying the pull force along the capsule sheath 102, the distance between the registration marks 304 and 305, or the width of the registration mark 609 can be measured from the image 608, produced by the imaging element 602. A longitudinal displacement of the imaging element 602 within capsule shaped tip 601 can be calculated or otherwise determined, as described herein above (cf. the displacement calculation 506). The longitudinal displacement can be processed by the computer program stored in data storage device 605 to control the longitudinal actuator 603 and translate the imaging element 602 so as to compensate the longitudinal displacement caused by the pull force along the capsule sheath.

Figure 7:
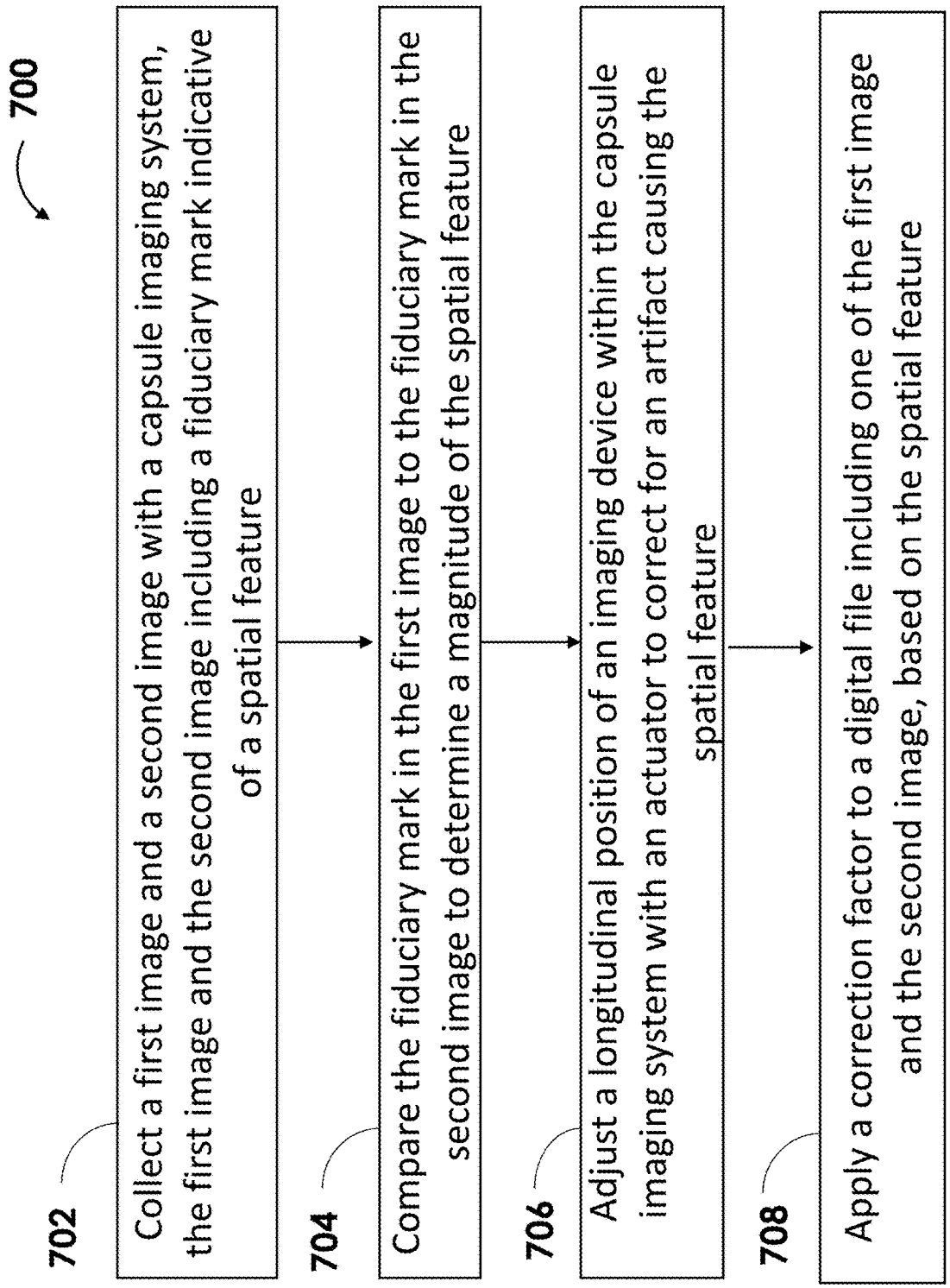
FIG. 7 is a flowchart illustrating steps in a method of forming an image with a capsule imaging system, as disclosed herein.

FIG. 7 is a flowchart illustrating steps in a method 700 of forming an image with a capsule imaging apparatus and/or a capsule imaging system (cf. capsule imaging apparatus 100 300, 500, and the capsule imaging system 600), as disclosed herein. In some embodiments, the steps in method 700 may be performed by a processor in a computer, executing instructions stored in a memory or data storage device, as disclosed herein (cf. processor 604 and memory 605). The computer may further include one or more displays and an I/O device (cf. display 606 and I/O 607). In some embodiments, methods consistent with the present disclosure may include at least one or more of the steps in method 700, performed in a different order, simultaneously, almost simultaneously, or overlapping in time.

Step 702 includes collecting a first image and a second image with the capsule imaging system. The first image and the second image may include a fiduciary mark indicative of a spatial feature (e.g., registration marks 301, 304, and 305).

Step 704 includes comparing the fiduciary mark in the first image to the fiduciary mark in the second image to determine a magnitude of the spatial feature. In some embodiments, the fiduciary mark comprises a first feature and a second feature, and the method further comprises measuring a distance between the first feature and the second feature. Step 704 includes comparing the distance between the first feature and the second feature in the first image and in the second image. In some embodiments, step 704 includes determining a magnitude of a pull force on a capsule containing the imaging device. In some embodiments, step 704 includes determining, with a controller, a degree of tension of a tether mechanically supporting the capsule imaging system based on the magnitude of the spatial feature. In some embodiments, step 704 further includes determining, with a controller, a force measurement on the capsule imaging system based on the magnitude of the spatial feature.

Step 706 includes adjusting a longitudinal position of an imaging device within the capsule imaging system with an actuator to correct for an artifact causing the spatial feature.

Step 708 includes applying a correction factor to a digital file including one of the first image and the second image, based on the spatial feature. In some embodiments, step 708 includes identifying a peristaltic motion of a distal tissue based on the magnitude of the spatial feature. In some embodiments, step 708 includes storing the magnitude of the spatial feature over a period of time and identifying a physiological rhythm associated with the spatial feature. In some embodiments, step 708 includes determining a longitudinal position of the imaging apparatus along a lumen of a bodily organ based on the fiduciary mark. In some embodiments, step 708 includes aligning a frame of the first image with a frame of the second image based on the fiduciary mark. In some embodiments, step 708 includes identifying a rotational distortion based on the fiduciary mark.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and paragraphs thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

What is claimed is:

1. An imaging apparatus, comprising:
   a capsule having a first end and a second end opposite to the first end;
   a sheath, mechanically coupled with the first end, and associated with a catheter body;
   an imaging element positioned between the first end and the second end, wherein the imaging elements includes one or more components to provide imaging radiation to a distal tissue and to collect a collect scattered radiation from the distal tissue; and
   registration markers, wherein;
      at least two of the registration markers are:
         (i) linear;
         (ii) disposed on the capsule;
         (iii) oriented diagonally with respect to two transverse planes of the capsule and along a partial circumference of the capsule having respective end points originating between the two transverse planes of the capsule, wherein at least one of the end points of each of the two of the two diagonally oriented registration markers connect and terminate at a common, intersection point; and
         (iv) configured to provide at least one fiduciary mark for each full rotation of the imaging element in an image formed with the scattered radiation.

2. The imaging apparatus of claim 1, wherein a terminal portion of the capsule at the first end has a tapered end that has a section that curves toward a center of the terminal portion.

3. The imaging apparatus of claim 1, wherein the sheath houses a torque coil configured to provide a rotating motion to the imaging element.

4. The imaging apparatus of claim 1, further comprising a window to protect the imaging element from the distal tissue, the window being transparent to the imaging radiation and to the scattered radiation.

5. The imaging apparatus of claim 1, wherein the registration markers comprise
   at least two of the registration markers are:
      separated by a distance indicative of a longitudinal position of the imaging element relative to the first end and the second end.

6. The imaging apparatus of claim 1, wherein the second end has an enlarged end portion that has a width that is greater than a width of the first end to facilitate a pull of the imaging apparatus through anatomical restrictions in the distal tissue.

7. The imaging apparatus of claim 1, wherein the sheath encloses an optical drive shaft optically coupled to the imaging element, the optical drive shaft configured to transmit the imaging radiation from a radiation source to the imaging element and to transmit the scattered radiation from the imaging element to a detector.

8. The imaging apparatus of claim 1, further comprising an outer sleeve that at least partially encloses the sheath.

9. The imaging apparatus of claim 1, wherein the sheath includes a lubricious material that facilitates at least one of a rotation or a translation of an optical drive shaft that provides a radiative coupling of the imaging element with a radiation source and with a detector.

10. The imaging apparatus of claim 1, wherein at least one portion of the sheath has at least one of a ridge or a groove with a helical configuration in a longitudinal direction.

11. The imaging apparatus of claim 1, wherein the sheath comprises:
   a first portion which is rigid, and a second portion which is flexible, wherein the sheath extends along a longitudinal direction and at least partially covers an optical drive shaft optically coupling the imaging element with an optical source and a detector.

* * * * *